United States Patent [19]
Gogolewski et al.

[11] Patent Number: 5,676,699
[45] Date of Patent: Oct. 14, 1997

[54] BONE REGENERATION MEMBRANE

[75] Inventors: Sylwester Gogolewski, Alvaneu-Dorf, Switzerland; Richard P. Meinig, Colorado Springs, Colo.; Stephan M. Perren, Davos, Switzerland

[73] Assignee: Laboratorium für experimentalle Chirurgie, Forschungsinstitut, Davos, Switzerland

[21] Appl. No.: 57,460

[22] Filed: May 7, 1993

Related U.S. Application Data

[63] Continuation of Ser. No. 580,180, Sep. 10, 1990, abandoned.
[51] Int. Cl.$^6$ ............................................. A61F 2/28
[52] U.S. Cl. ........................................ 623/16; 623/66
[58] Field of Search .................... 623/1, 11, 12, 623/16, 66

[56] References Cited

U.S. PATENT DOCUMENTS

| | | | |
|---|---|---|---|
| 3,710,789 | 1/1973 | Ersek | 623/16 |
| 3,901,810 | 8/1975 | Brooks et al. | 210/500.28 |
| 3,938,515 | 2/1976 | Leeper et al. | 424/432 |
| 4,011,602 | 3/1977 | Rybicki et al. | 623/16 |
| 4,309,488 | 1/1982 | Heide et al. | 606/76 |
| 4,550,449 | 11/1985 | Tunc | 623/16 |
| 4,637,931 | 1/1987 | Schmitz | 623/16 |
| 4,674,488 | 6/1987 | Nashef et al. | 606/76 |
| 4,795,467 | 1/1989 | Piez et al. | 623/16 |
| 4,842,604 | 6/1989 | Dorman et al. | 423/16 |
| 4,863,472 | 9/1989 | Törmälä et al. | 623/16 |
| 4,963,145 | 10/1990 | Takagi et al. | 606/76 |
| 5,007,930 | 4/1991 | Dorman et al. | 623/16 |
| 5,024,841 | 6/1991 | Chu et al. | 604/890.1 |
| 5,250,584 | 10/1993 | Ikada et al. | 623/16 |

FOREIGN PATENT DOCUMENTS

| | | | |
|---|---|---|---|
| 0011528 | 5/1980 | European Pat. Off. | 606/77 |
| 0295041 | 12/1988 | European Pat. Off. | 606/60 |
| 0321442 | 6/1989 | European Pat. Off. | |
| 0349505 | 1/1990 | European Pat. Off. | |
| 2815934 | 10/1979 | Germany | 606/76 |
| 1170001 | 7/1984 | Switzerland | |
| 2215209 | 9/1989 | United Kingdom | 606/77 |
| 88/08305 | 11/1988 | WIPO | |
| 90/13302 | 11/1990 | WIPO | |

OTHER PUBLICATIONS

I. Magnusson et al, "New Attachment Formation Following Controlled Tissue Regeneration Using Biodegradable Membranes", *J. Periodontol*, Jan. 1988, pp. 1–5.

Farsø–Nielsen et al, "Healing of Radial Bone Defects in Rabbits Using Biodegradable Membranes", IADR/AADR General Session, Mar. 7–11, 1990, Cincinnati, Ohio.

Christer Dahlin et al, "Healing of Bone Defects by Guided Tissue Regeneration", *Plastic and Reconstructive Surgery*, vol. 81, No. 5, May 1988, pp. 672–676.

*Primary Examiner*—Debra S. Brittingham
*Attorney, Agent, or Firm*—Karen Lee Orzechowski; Walter C. Farley; Nath & Associates

[57] ABSTRACT

A bone regeneration membrane containing resorbable or degradable, polymeric and/or polymeric-ceramic material with a glass transition temperature in the range of −30° to +200° C.

The novel membrane can be used for the spontaneous regeneration of bone and for the improved application of autologous or allogenic graft materials and therapeutic agents.

30 Claims, 2 Drawing Sheets

BONE REGENERATION MEMBRANE

This application is a file wrapper continuation of application Ser. No. 580,180 filed on Sep. 10, 1990, now abandoned.

BACKGROUND OF THE INVENTION

1. Field of the Invention

This invention relates to a bone regeneration membrane containing resorbable or degradable polymeric and/or polymeric-ceramic material.

Diaphyseal bone loss results from high-energy trauma, infection, or resection performed for skeletal neoplasia. The numerous treatment modalities attest to the difficulty in obtaining reliable and satisfactory reconstitution of skeletal long bone defects. Methods for treating diaphyseal bone defects include: autologous cancellous or cortical bone grafts, autologous vascularized bone transplants and grafts, xenogenic bone grafts, allogenic bone grafts, hydroxyapatite and/or tricalcium phosphate ceramics implants, coral, natural polymers like collagen, synthetic polymers like polyethylene and polyglycolide, osteoinductive proteins such as bone morphogenetic protein, and bone transport techniques. All these methods have failed in producing predictable reconstruction of cortico-cancellous bone loss from diaphyseal segment of the human skeleton.

2. Description of the Prior Art

Various proposals have been made for the application of membranes containing resorbable or degradable polymeric material for bone regeneration purposes. These membranes degrade in the body over a period of time and may be absorbed by the bone or body tissues.

From an article of Magnusson, Batich and Collins, published in the J. Periodontol., Jan. 1988 pp. 1–5, it is known to utilize very thin membranes of unspecified porosity and consisting of low-molecular weight polylactic acid for the regeneration of the dental cementum.

It is also known from Dahlin, Linde, Gottlow and Nyman (Plastic and Reconstructive Surgery, May 1988, pp. 672–676) to use a porous polytetrafluoroethylene membrane for healing bone in the jaw.

It is further known from Farso-Nielsen, Karring and Gogolewski (IADR General Session, Mar. 7–11, 1990, Cincinnati, Ohio) to use elastic biodegradable polyurethane membranes of unspecified structure for healing bone defects in rabbits.

From Warrer, Karring, Nyman and Gogolewski (paper submitted to J.Periodontol. 1990) it is further known that the use of membranes consisting of unspecified polylactic acid or polyurethane polymers failed to produce regeneration of periodontal defects.

With all these prior art membranes of largely unspecified structure and chemistry clinical results are rather unpredictable and vary from author to author.

SUMMARY OF THE INVENTION

The present invention is intended to remedy these drawbacks. It solves the problem of how to design a membrane containing resorbable or degradable polymeric and/or polymeric-ceramic material having a well-defined structure and chemistry which—when properly fashioned and applied—will promote spontaneous human bone regeneration as well as improve the efficacy of adjunctive bone conductive and inductive substances.

Briefly described, the invention comprises a bone regeneration membrane containing resorbable or degradable polymeric and/or polymeric-ceramic material having a glass transition temperature in the range of $-30°$ C. to $200°$ C., the membrane having micropores therein. At least 90 percent of the micropores have a diameter in the range of 0.001 to 50.0 μm and the overall porosity of the membrane is less than 90 percent.

The membrane advantage contains osteoconductive or osteoinductive agents of autogenic, allogenic, xenogenic or synthetic origin.

The polymeric or polymeric-ceramic material used for the membranes according to the invention must have the glass transition temperature in the range of $-30°$ to $+200°$ C., Preferably the glass transition temperature of said polymeric and/or polymeric-ceramic material is in the range of $+10°$ to $+90°$ C. and most preferably between $+30°$ to $+70°$ C.

Glass transition temperature has surprisingly turned out to be of great importance, since application of membranes made of low glass transition temperature polymeric materials to bone defects have resulted in undesired external callus formation.

Chemically the membrane is prepared from highly purified resorbable and/or degradable polymers and/or polymer-ceramics such as polyhydroxyacids, polysaccharides, polyamines, polyaminoacids, polyorthoesters, polyanhydrides, collagen or composites thereof with tricalcium phosphate and/or hydroxyapatite, whereby preferably at least 90 weight percent of the material has a molecular weight in the range of 5,000 to 1,000,000, preferably in the range of 25,000 to 150,000 and most preferably in the range of 30,000 to 70,000.

In terms of molecular weight distribution, (or polydispersity) the polymeric and/or polymeric-ceramic material should have a polydispersity in the range of 1.2 to 100.0, preferably in the range of 1.9 to 2.5.

Structurally the membrane is generally thin and preferably microporous. The thickness of the membrane can be controlled to meet structural demands of the proposed implantation site, but should range between 0.05 to 5.0 mm, preferably between 0.2 to 3.0 mm and most preferably between 0.4 to 1.5 mm. The specific pore size, shape and structure to be selected for a certain application is variable to a large extent, whereby at least 90 percent of the micropores present in the polymeric material should have a diameter below 500 μm, preferably in the range of 0.01 to 50.0 μm and most preferably in the range of 0.1 to 5 μm. What is essential is that the micropores are permeable for nutritional fluids. Therefore the micropores within the membrane should be preferably interconnected to allow liquids penetration and circulation.

A membrane having the structural and chemical features according to the invention exhibits a resorption rate in vivo in the range from 2 weeks to 1 year and longer. The resorption rate can be adjusted to a desired value (e.g. to over one year for the treatment of large defects) by altering the polymer molecular weight, the polymer chain orientation and crystallinity, physical structure, chemical composition, presence and extent of voids, additives and so on.

The membranes can be used in a planar form, but generally are prefashioned or modified intraoperatively by the surgeon to conform to a curved surface, preferably a rectilinear surface. Most suitable are membranes with an adaptable surface, preferably a cylindrical surface, which most preferably is of tubular (circular cylinder) form.

In a preferred embodiment the membrane according to the invention is shaped in tubular form, preferably with a longitudinal slit to allow variability of the tubular diameter over a wide range. The diameter of the tubular membrane should match the dimensions of the bone to be treated, e.g. 4.0 to 50.0 mm for tibia reconstructions. A thin membrane of e.g. 0.1 mm thickness can also be rolled up either pre- or intraoperatively to form a final tubular implant with a wall thickness of e.g. 3.1 mm.

In a preferred embodiment the overlapping, intersected tubular membrane according to the invention provides semi-occlusive fits at the two extremities of the tube for better external adaptation to the cortical bone ends and/or internal adaptation within medullary canals of long or tubular bones.

It is of importance that the internal membrane tube to be inserted into an intramedullary canal is formed on a mandrel which has an external diameter at least 1.1 to 3.0 times bigger than the diameter of the intramedullary canal. The external membrane tube should be formed on a mandrel which has an external diameter which is at least 1.1 to 3.0 times smaller than the external diameter of the bone. Due to its "shape memory" the tubular membrane can be easily placed and fit on the bone to be treated.

If two tubular membranes are used (an external over the cortical bone ends and a internal within the medullary canal) they can either be used with or without spacers between the two tubular membranes. The two membranes can either be supplied preoperatively as a single unit (with interconnecting structures) or can be assembled intraoperatively by the surgeon. Accordingly one membrane is rolled in a tubular fashion to obtain a press fit into the medullary canal of both bone fragments, and a second membrane is rolled into a tube to form a semi-occlusive external sleeve, bridging the two bone fragment ends. The space between the two membranes forms a new artificial cortex that can be filled with a variety of therapeutic substances, such as autologous bone, allogenic bone, demineralized bone powder extracts, bone morphogenetic protein isolates, antibiotics, or antineoplastic drugs. The walls of the membranes can either be continuous or intersected longitudinally for better adaptation of the membrane on the bone. If necessary, the space between the inner and outer tubular membranes can be maintained in their relative position by means of spokes, ribs or other corrugated elements attached permanently, or inserted between the membrane tubes upon surgery.

The membrane tube can be used as a complete construction or only as a part of the construction (e.g. a half construction) depending on the bone defect to be treated.

The membranes according to the invention can be used for a variety of applications to span osseous defects that have been conventionally stabilized with an external fixator, intramedullary rod, or systems of plates and screws, of which the most important are listed below:

- as a tissue separator which promotes and protects osseous regeneration;
- for the treatment of osseous defects secondary to trauma, infection, neoplasm, or surgical resection;
- as cortical spacer across bone defects;
- as an osseous activity barrier that confines bone regeneration to desired regions and prevents the formation of synostosis, physeal bars, or ectopic bone;
- as a spacer for skeletal resection, revision arthroplasty, or arthrodesis of human joints;
- as a container for autologous or allogenic graft materials; and
- as a combined bone grafting and/or drug delivery system.

The membrane according to the invention, therefore, offers a novel treatment that reliably promotes osseous healing with and without adjunctive therapies, while posing no toxic risks or requirements for extensive surgery for implantation or removal. The membrane can be preoperatively shaped and adjusted by the surgeon to conform and integrate with a wide range of anatomical defects and locations.

The advantages offered by the invention are mainly the following:

- maintainance of a physical barrier that contains osseous activity of the host bone, while simultaneously protecting this osseous activity from nonosteogenic and interfering cell lines.
- protection of the cortical and medullary canal osteogenic capacity from surrounding soft tissues and inflammatory reactions.

BRIEF DESCRIPTION OF THE DRAWINGS

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

In the drawings.

DESCRIPTION OF THE PREFERRED EMBODIMENTS

The membranes according to the invention can be produced by any technique known to those skilled in the art, e.g. by solvent-casting, extrusion, injection-moulding, vacuum-forming, blowing, spraying, brushing, polymerization, compression-moulding, etc.

Two specific examples are given below:

EXAMPLE I

Poly(L-lactide) with a viscosity-average molecular weight in the range of 15,000–700,000 Daltons were purified twice by dissolution in chloroform followed by precipitation with methanol. Polymers were dried under vacuum to constant weight and kept in a dessicator over molecular sieves. Microporous, resorbable membranes were prepared in the phase-reverse technique. Flat membranes were wetted in polar or nonpolar liquids and preshaped over mandrels of suitable shape, to fit the approximate diameter of the implantation site. The membranes were preshaped to the anatomy of the bone to be covered.

Figure 1:
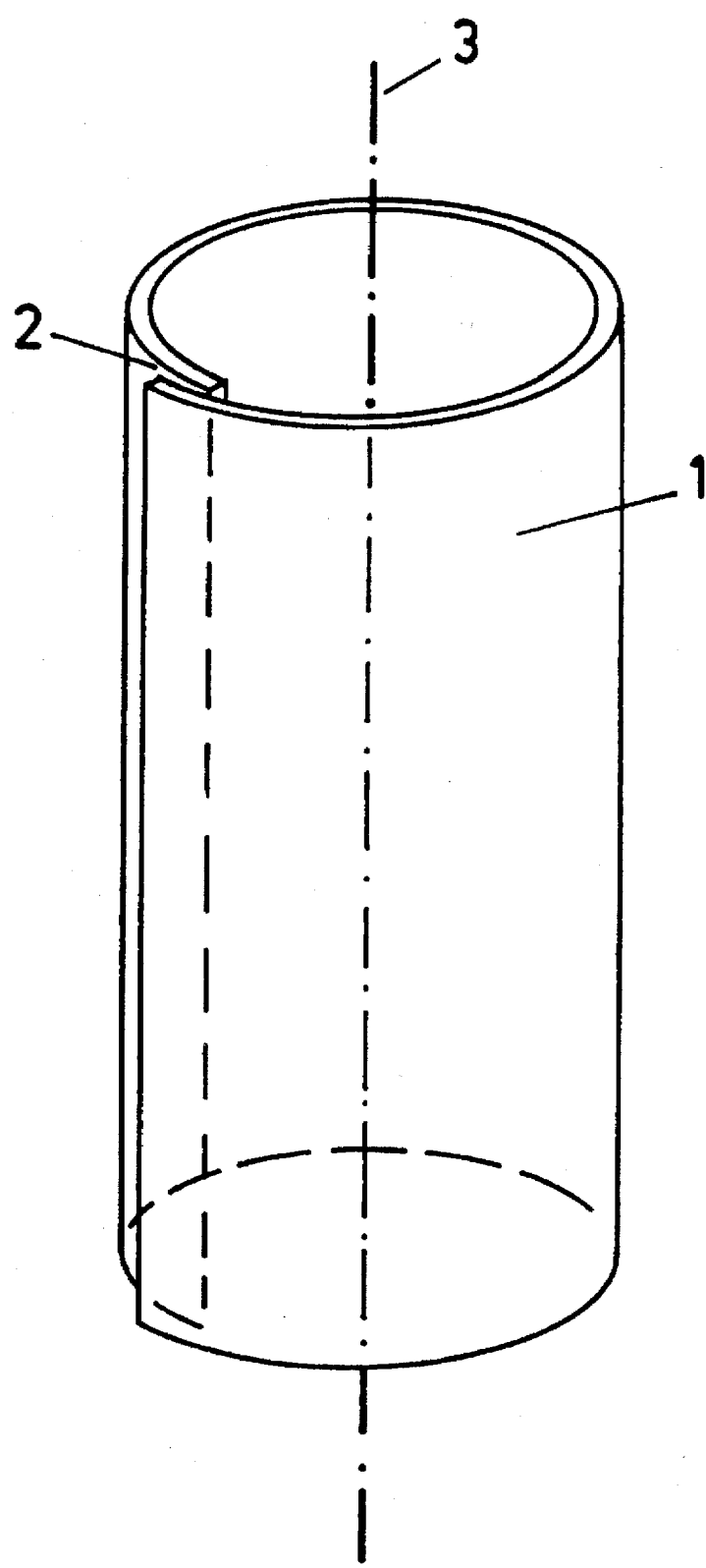
FIG. 1 is a simplified perspective view of a membrane in accordance with the invention.

Wet membranes rolled up on the mandrels were covered with aluminium foil to protect them against unrolling and placed at 50°–150° C. in the vacuum oven for 0.5–6.0 hours. After removal of the aluminium foil the membrane 1 had the configuration as shown in FIG. 1. Thanks to the longitudinal slit 2 parallel to its central axis 3 and its inherent shape memory the membrane was adaptable in diameter over a large extent to match bone ends of different sizes and diameters. The membrane produced according to this example had a glass transition temperature of +50° C., The pore size of the membrane was in the range of 0.1 to 1.0 μm and its thickness was 1.0 mm. Viscosity—average molecular weight of the polymeric membrane according to this example was 75,000, and its molecular weight distribution was 2.2.

The tubular membranes were used to cover a diphyseal defect of ten rabbits, Two months after surgery the canal created by the membrane according to this example was filled with osseous tissue.

EXAMPLE II

Microporous resorbable membranes were prepared from poly(L-lactide) with a viscosity-average molecular weight of 15,000 to 100,000 Daltons according to the method of manufacture described in Example I.

The membrane produced according to this example had a glass transition temperature of 50° C. and showed a porosity in the range of 10 to 50 μm and a thickness of 0.9 mm.

Numerous controlled experiments by the applicants have demonstrated that the novel membranes obtained by the described methods of manufacture promote bone growth in a reliable manner and further improve the efficacy of adjunctive bone conductive and inductive substances.

The membrane obtained by the method according to Example II was sterilized with ethylene oxide and implanted in 15 mature rabbits, to cover mid-diaphyseal defects of 10 mm created in the radius of a limb. An identical, but untreated defect on the other limb served as a control.

Within one week the membrane implants were filled with tissues that progressively differentiated into osseous tissue. By one month, further osseous formation had bridged 40 to 95% of the defect. New bone was formed within the inner canal of the polymeric membrane tube. In contrast, the control defects were occupied by overlying muscle and soft tissues.

Figure 2:
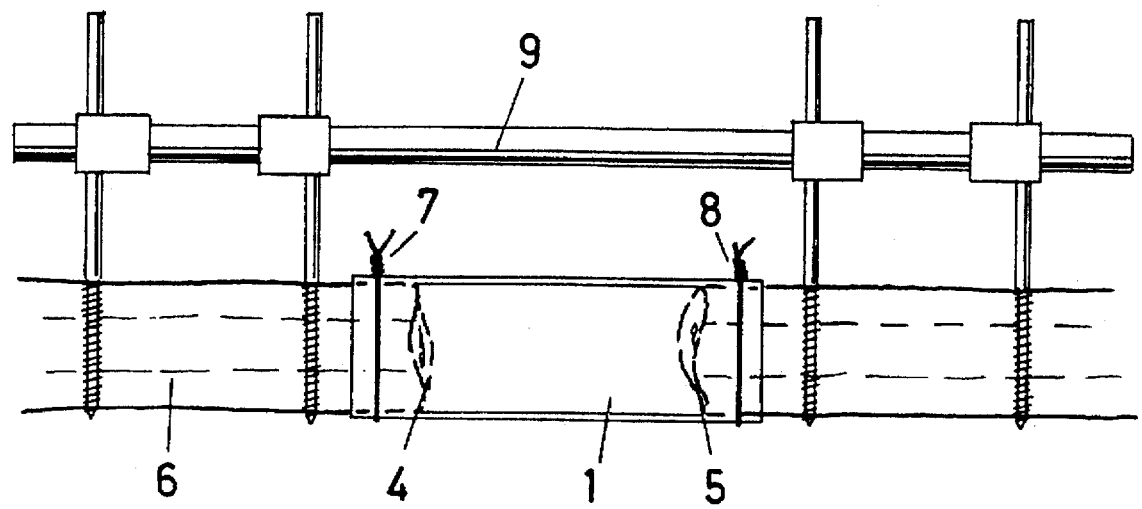
FIG. 2 is a side elevation schematically illustrating technique for applying a membrane in accordance with the invention.

The application of the membranes according to the invention is now further described by having reference to the drawings:

In a first application, shown in FIG. 2, a tubular membrane 1 was pulled over the aligned and correctly positioned extremities 4,5 of a fractured long bone 6 and affixed thereto by means of wires 7,8. Of course the membrane 1 can be affixed to the bone ends 4,5 by a variety of suitable means including external suture, metal or polymer screws, and/or plate and band combinations. The whole assembly was further fixed by means of an external fixator 9.

Figure 3:
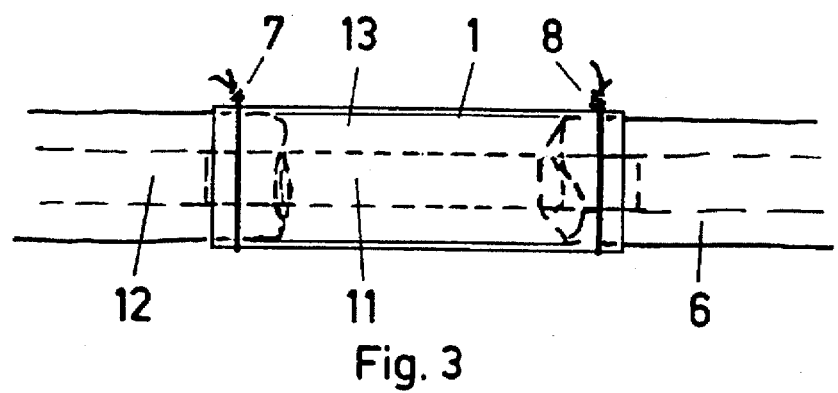
FIG. 3 is a side elevation schematically illustrating an application of membranes in the intermedullary canal as well as externally.
Figure 4:
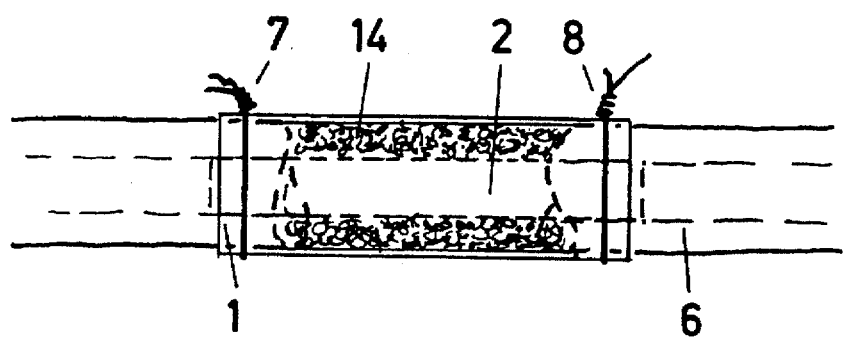
FIG. 4 is an illustration of an application similar to FIG. 3 wherein the space between membranes is filled with autogenic cancellous bone graft.

In a second application, shown in FIG. 3, prior to the fixation of the external membrane 1, a second tubular membrane 11 was previously inserted in the intramedullary canal 12, thereby forming a confined space 13, which as shown in FIG. 4 was filled with autogenic cancellous bone graft 14.

We claim:

1. A thin, resorbable bone regeneration membrane containing interconnected micropores and having a thickness between 0.05 mm and 5.0 mm, said membrane comprising resorbable or degradable polymeric material wherein the glass transition temperature of said polymeric material is in the range of body temperature to 200° C. and the molecular weight distribution of said polymeric material is in the range of 1.2 to 100.0.

2. A membrane according to claim 1 where said glass transition temperature of said polymeric and/or polymeric-ceramic material is in the range of body temperature to +90° C.

3. A membrane according to claim 1 wherein at least 90 percent of said micropores have a diameter in the range of 0.1 to 5.0 μm.

4. A membrane according to claim 1 wherein at least 90 weight percent of said polymeric material has a molecular weight in the range of 5,000 to 1,000,000.

5. A membrane according to claim 1 wherein at least 90 weight percent of said polymeric material has a molecular weight in the range of 25,000 to 150,000.

6. A membrane according to claim 5, wherein said polymeric material is selected from the group consisting of highly purified polyhydroxyacids, polysaccharides, polyamines, polyaminoacids, polyorthoesters, polyanhydrides, collagen, and composites thereof with tricalcium phosphate and/or hydroxyapatite.

7. A membrane according to claim 1, which further contains antibiotic agents.

8. A membrane according to claim 1, which has a curved surface.

9. A membrane according to claim 8, wherein said curved surface is capable of being adapted to match the dimensions of the bone.

10. A membrane according to claim 16, which has a shape memory.

11. A membrane according to claim 9, wherein said membrane is formed into a tubular form with a longitudinal slit.

12. A membrane according to claim 11 comprising a sheet for use in surgical procedures, wherein said sheet is fashioned into a tubular form intraoperatively by the surgeon.

13. A membrane according to claim 11, comprising a sheet rolled up to form a multilayer tube.

14. A membrane according to claim 2 wherein said glass transition temperature is in the range of +40° C. to +70° C.

15. A membrane according to claim 1 wherein at least 99 weight percent of said polymeric material has a molecular weight in the range of 5,000 to 1,000,000.

16. A membrane according to claim 1 and having a thickness between 0.2 mm and 3.0 mm.

17. A membrane according to claim 16 and having a thickness of between 0.4 mm and 1.5 mm.

18. A membrane according to claim 5 wherein at least 90 weight percent of said polymeric material has a molecular weight in the range of 30,000 to 70,000.

19. A membrane according to claim 8, wherein said membrane has a surface defined by the movement of a substantially straight line along a curved planar path.

20. A membrane according to claim 9 wherein said surface is cylindrical.

21. A membrane according to claim 12 wherein said tubular form is adapted to be modified intraoperatively by a surgeon applying said membrane to match the dimensions of the bone.

22. A membrane according to claim 1 wherein said polymeric material has a molecular weight distribution in the range of 1.9 to 2.5.

23. A bone regeneration membrane comprising resorbable or degradable polymeric and/or polymeric-ceramic material wherein the glass transition temperature of said polymeric and/or polymeric-ceramic material is in the range of body temperature to 200° C. and the molecular weight distribution of said polymeric material is in the range of 1.2 to 100.0, said membrane having interconnected micropores therein, and further comprising reinforcement including resorbable and/or degradable fibers.

24. A bone regeneration membrane comprising resorbable or degradable polymeric and/or polymeric-ceramic material wherein the glass transition temperature of said polymeric and/or polymeric-ceramic material is in the range of body temperature to 200° C. and the molecular weight distribution of said polymeric material is in the range of 1.2 to 100.0, said membrane having interconnected micropores therein, wherein said membrane further contains antiosteomyelitis agents.

25. A bone regeneration membrane comprising resorbable or degradable polymeric and/or polymeric-ceramic material wherein the glass transition temperature of said polymeric and/or polymeric-ceramic material is in the range of body temperature to 200° C. and the molecular weight distribution of said polymeric material is in the range of 1.2 to 100.0, said membrane having interconnected micropores therein, wherein said membrane further contains antineoplastic agents.

26. A bone regeneration membrane comprising resorbable or degradable polymeric and/or polymeric-ceramic material wherein the glass transition temperature of said polymeric and/or polymeric-ceramic material is in the range of body temperature to 200° C. and the molecular weight distribution of said polymeric material is in the range of 1.2 to 100.0, said membrane having interconnected micropores therein, wherein said membrane further contains osteoconductive agents of autogenic, allogenic, xenogenic, or synthetic origin.

27. A bone regeneration membrane comprising resorbable or degradable polymeric and/or polymeric-ceramic material wherein the glass transition temperature of said polymeric and/or polymeric-ceramic material is in the range of body temperature to 200° C. and the molecular weight distribution of said polymeric material is in the range of 1.2 to 100.0, said membrane having interconnected micropores therein, wherein said membrane further contains osteoinductive agents of autogenic, allogenic, xenogenic, or synthetic origin.

28. A bone regeneration membrane comprising resorbable or degradable polymeric and/or polymeric-ceramic material wherein the glass transition temperature of said polymeric and/or polymeric-ceramic material is in the range of body temperature to 200° C. and the molecular weight distribution of said polymeric material is in the range of 1.2 to 100.0, said membrane having interconnected micropores therein, wherein said membrane is formed in a tubular form with a longitudinal slit adapted to form semi-occlusive fits at the two extremities of the tube formed by said membrane for fixation to bones.

29. A bone regeneration membrane comprising resorbable or degradable polymeric and/or polymeric-ceramic material wherein the glass transition temperature of said polymeric and/or polymeric-ceramic material is in the range of body temperature to 200° C. and the molecular weight distribution of said polymeric material is in the range of 1.2 to 100.0, said membrane having interconnected micropores therein, wherein said membrane is formed in a tubular form with a longitudinal slit having ends shaped to form semi-occlusive fits over cortical bone ends and within medullary canals of long or tubular bones.

30. A thin, resorbable bone regeneration membrane containing interconnected micropores and having a thickness between 0.05 mm and 5.0 mm, said membrane consisting of resorbable or degradable polymeric material having a glass transition temperature in the range of body temperature to 200° C. and the molecular weight distribution of said polymeric material is in the range of 1.2 to 100.0.

* * * * *